(12) United States Patent
Kodama et al.

(10) Patent No.: US 11,759,123 B2
(45) Date of Patent: Sep. 19, 2023

(54) KETONE BODY CONCENTRATION ESTIMATION DEVICE, METHOD, AND COMPUTER-READABLE STORAGE MEDIUM

(71) Applicant: Tanita Corporation, Tokyo (JP)

(72) Inventors: Miyuki Kodama, Tokyo (JP); Ayumi Kusama, Tokyo (JP); Yasuhiro Kasahara, Tokyo (JP); Naotaka Minagawa, Tokyo (JP)

(73) Assignee: Tanita Corporation, Tokyo (JP)

( * ) Notice: Subject to any disclaimer, the term of this patent is extended or adjusted under 35 U.S.C. 154(b) by 1313 days.

(21) Appl. No.: 15/918,404

(22) Filed: Mar. 12, 2018

(65) Prior Publication Data

US 2018/0263529 A1 Sep. 20, 2018

(30) Foreign Application Priority Data

Mar. 15, 2017 (JP) .................... 2017-050416

(51) Int. Cl.
*A61B 5/083* (2006.01)
*A61B 5/08* (2006.01)
*G01N 33/64* (2006.01)
*A61B 5/097* (2006.01)

(52) U.S. Cl.
CPC ............ *A61B 5/0833* (2013.01); *A61B 5/082* (2013.01); *A61B 5/083* (2013.01); *G01N 33/64* (2013.01); *A61B 5/097* (2013.01)

(58) Field of Classification Search
CPC ....... A61B 5/0833; A61B 5/082; A61B 5/083; G01N 33/64
See application file for complete search history.

(56) References Cited

U.S. PATENT DOCUMENTS

| | | | | |
|---|---|---|---|---|
| 4,970,172 A | * | 11/1990 | Kundu | A61B 5/083 436/130 |
| 5,071,769 A | * | 12/1991 | Kundu | A61B 5/083 436/178 |
| 5,174,959 A | * | 12/1992 | Kundu | G01N 33/64 436/128 |
| 2013/0288208 A1 | | 10/2013 | Yamada et al. | |
| 2015/0212062 A1 | | 7/2015 | Kodama et al. | |

FOREIGN PATENT DOCUMENTS

| | | |
|---|---|---|
| CN | 103503016 A | 1/2014 |
| JP | 2014-188267 A | 10/2014 |
| JP | 2015-167575 A | 9/2015 |

OTHER PUBLICATIONS

Extended European Search Report issued in corresponding European Patent Application No. 18161175.7 dated Jul. 24, 2018.
Office Action issued in related Chinese Patent Application No. 201810205217.4 dated Jun. 20, 2022.

* cited by examiner

*Primary Examiner* — Jerry Lin
(74) *Attorney, Agent, or Firm* — Morgan, Lewis & Bockius LLP

(57) ABSTRACT

An acetone concentration estimate device acquires a measured acetone concentration measuring acetone excreted from a user, acquires an elapsed time which has elapsed since the user ate a meal, and estimates an acetone concentration, which is a ketone body concentration of when an amount of change in blood sugar level of the user per given unit of time is stable, based on the acquired current measured acetone concentration and on the acquired elapsed time, and outputs information corresponding to the estimated acetone concentration.

19 Claims, 7 Drawing Sheets

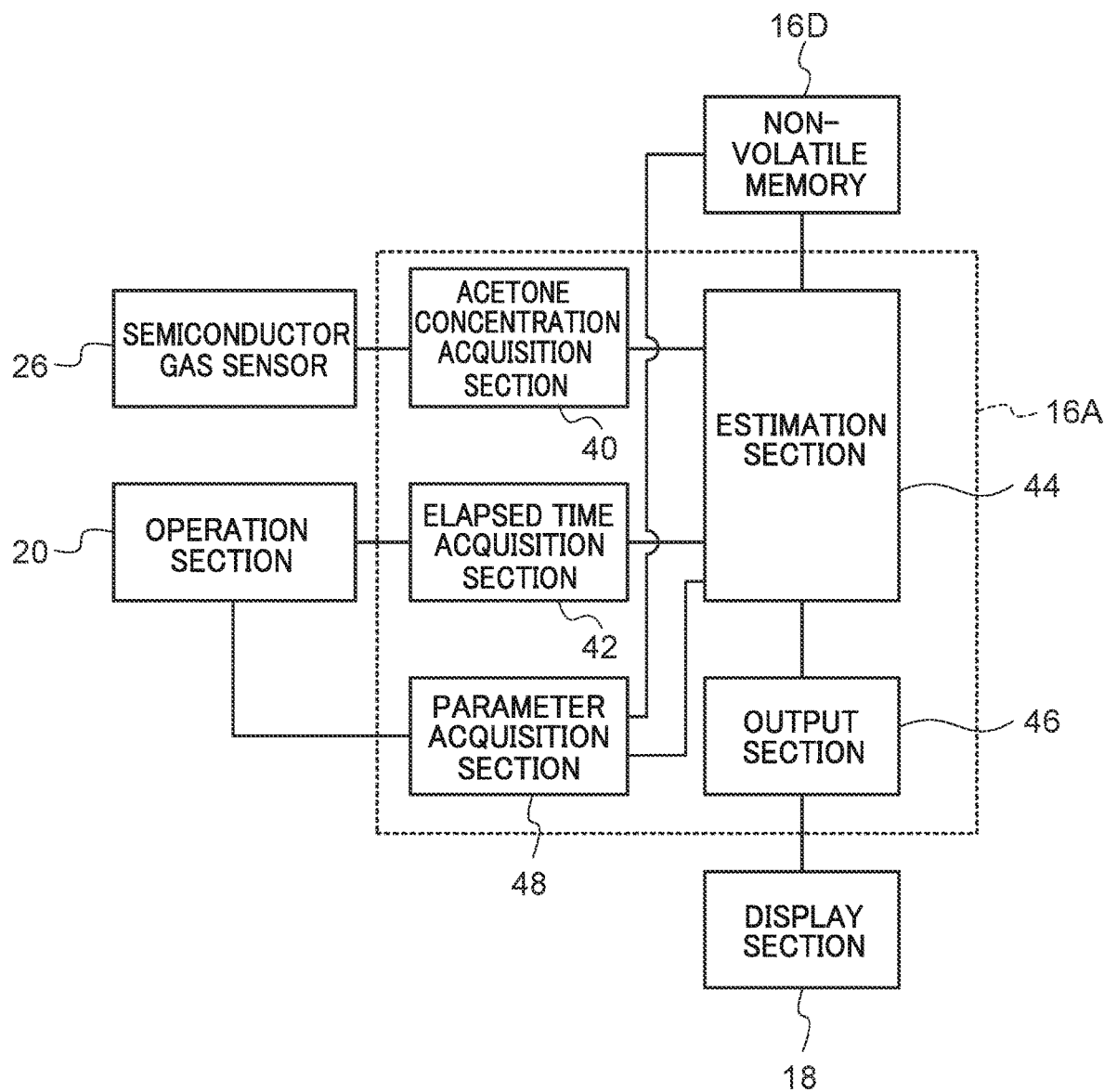

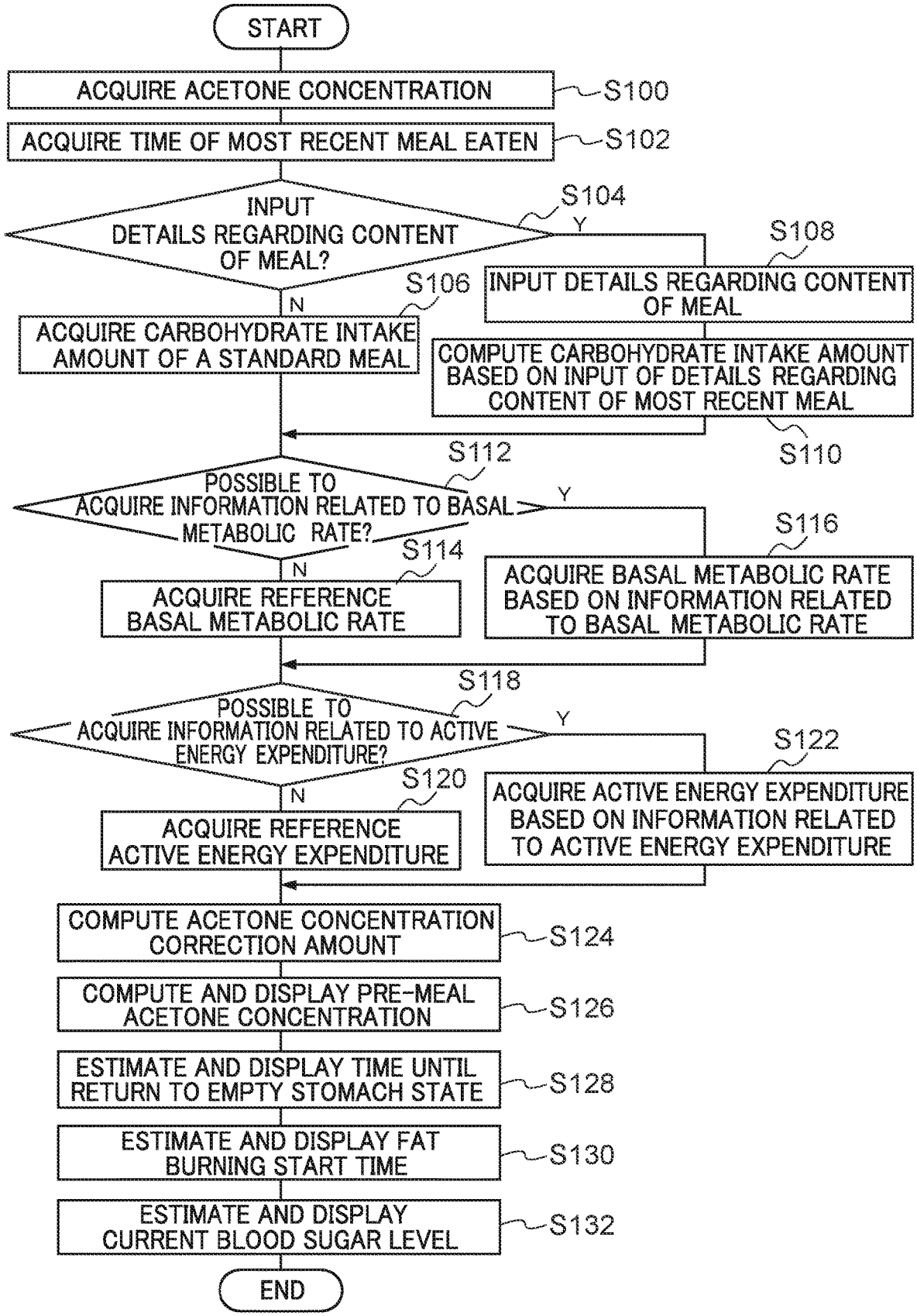

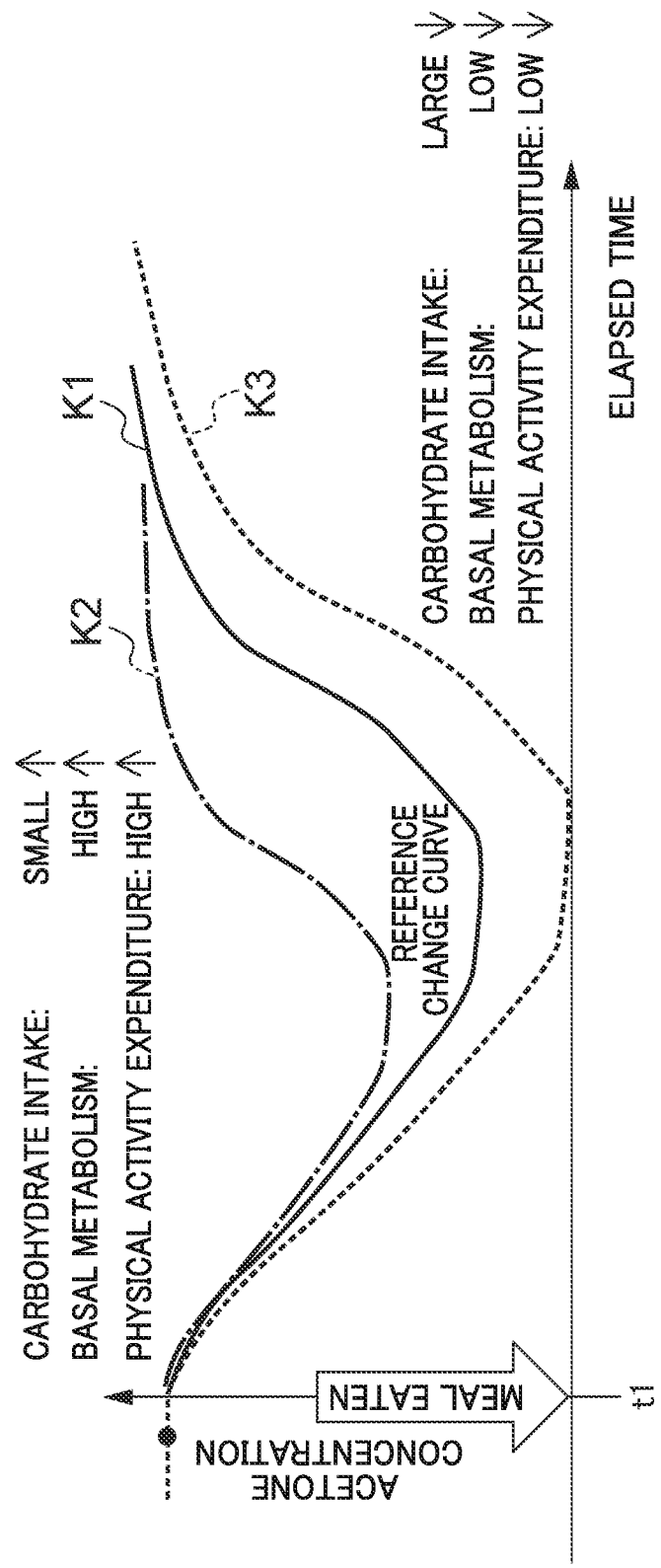

FIG.6

| ACETONE CONCENTRATION AT ELAPSED TIME A | CARBOHYDRATE INTAKE AMOUNT B | BASAL METABOLIC RATE C | ACTIVE ENERGY EXPENDITURE D | CORRECTION EQUATION |
|---|---|---|---|---|
| f(A) | LOW (B < α1) | LOW C < x1 | D < x4 | f(A) −f1 (B,C,D) |
| | | | x4 < D ≤ x5 | f(A) −f2 (B,C,D) |
| | | | x5 < D ≤ x6 | f(A) −f3 (B,C,D) |
| | | | x6 < D ≤ x7 | f(A) −f4 (B,C,D) |
| | | | x7 < D ≤ x8 | f(A) −f5 (B,C,D) |
| | | MEDIUM x1 ≤ C < x2 | D < x4 | f(A) −f6 (B,C,D) |
| | | | x4 < D ≤ x5 | f(A) −f7 (B,C,D) |
| | | | x5 < D ≤ x6 | f(A) −f8 (B,C,D) |
| | | | x6 < D ≤ x7 | f(A) −f9 (B,C,D) |
| | | | x7 < D ≤ x8 | f(A) −f10 (B,C,D) |
| | | HIGH x2 ≤ C | D < x4 | f(A) −f11 (B,C,D) |
| | | | x4 < D ≤ x5 | f(A) −f12 (B,C,D) |
| | | | x5 < D ≤ x6 | f(A) −f13 (B,C,D) |
| | | | x6 < D ≤ x7 | f(A) −f14 (B,C,D) |
| | | | x7 < D ≤ x8 | f(A) −f15 (B,C,D) |
| | MEDIUM (α1 ≤ B < α2) | LOW C < x1 | D < x4 | f(A) −f16 (B,C,D) |
| | | | x4 < D ≤ x5 | f(A) −f17 (B,C,D) |
| | | | x5 < D ≤ x6 | f(A) −f18 (B,C,D) |
| | | | x6 < D ≤ x7 | f(A) −f19 (B,C,D) |
| | | | x7 < D ≤ x8 | f(A) −f20 (B,C,D) |
| | | MEDIUM x1 ≤ C < x2 | D < x4 | Then, apply each corresponding equation |
| | | | x4 < D ≤ x5 | |
| | | | x5 < D ≤ x6 | |
| | | | x6 < D ≤ x7 | |
| | | | x7 < D ≤ x8 | |
| | | HIGH x2 ≤ C | D < x4 | |
| | | | x4 < D ≤ x5 | |
| | | | x5 < D ≤ x6 | |
| | | | x6 < D ≤ x7 | |
| | | | x7 < D ≤ x8 | |
| | HIGH (α2 ≤ B) | LOW C < x1 | D < x4 | |
| | | | x4 < D ≤ x5 | |
| | | | x5 < D ≤ x6 | |
| | | | x6 < D ≤ x7 | |
| | | | x7 < D ≤ x8 | |
| | | MEDIUM x1 ≤ C < x2 | D < x4 | |
| | | | x4 < D ≤ x5 | |
| | | | x5 < D ≤ x6 | |
| | | | x6 < D ≤ x7 | |
| | | | x7 < D ≤ x8 | |
| | | HIGH x2 ≤ C | D < x4 | |
| | | | x4 < D ≤ x5 | |
| | | | x5 < D ≤ x6 | |
| | | | x6 < D ≤ x7 | |
| | | | x7 < D ≤ x8 | |

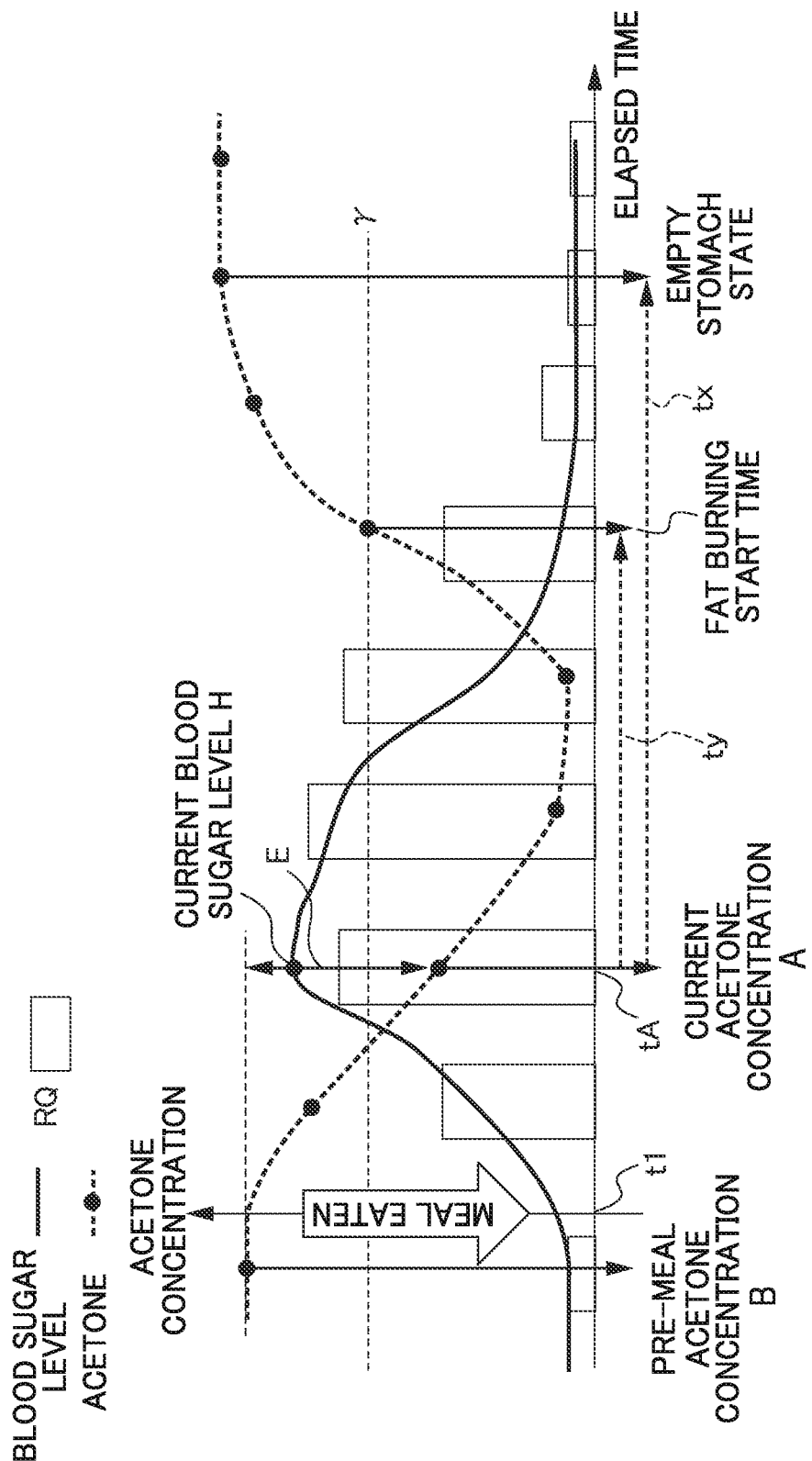

KETONE BODY CONCENTRATION ESTIMATION DEVICE, METHOD, AND COMPUTER-READABLE STORAGE MEDIUM

CROSS-REFERENCE TO RELATED APPLICATION

This application is based on and claims priority under 35 USC 119 from Japanese Patent Application No. 2017-050416 filed on Mar. 15, 2017, the entire contents of which is incorporated by reference herein.

BACKGROUND

Technical Field

The present invention relates to a ketone body concentration estimation device, method, and computer-readable storage medium.

Related Art

Japanese Patent Application Laid-Open (JP-A) No. 2015-167575 discloses technology in which a measurement of ketone body concentration measuring ketone bodies excreted from a user is acquired, and a fat burning ratio of visceral fat to subcutaneous fat for a user is computed based on the acquired current measurement of ketone body concentration, a measurement of ketone body concentration measured in the past, and the current visceral fat amount of the user. JP-A No. 2015-167575 further discloses that acetone, which is one type of ketone body, is a byproduct in the metabolism of fat, and that higher acetone concentrations can indicate increased metabolism of fat.

JP-A No. 2014-188267 discloses technology in which acetone concentration in a biological gas of a test subject is detected, and a metabolic state is analyzed based on the detected acetone concentration.

However, JP-A No. 2014-188267 describes post-meal acetone concentration gently decreasing even when a test subject is at rest, and acetone concentration being stable when the stomach is empty. Thus, the present inventors recognized that it is difficult to analyze a metabolic state of a test subject using a ketone body concentration measured after a meal has been eaten. Further, the present inventors recognized that there is room for improvement regarding improving the degrees of freedom in the timing to measure ketone body concentration to ascertain the metabolic state of a user in a steady state.

SUMMARY

An object of the present invention is to provide a ketone body concentration estimation device, method, and computer-readable storage medium capable of estimating a ketone body concentration of when an amount of change in blood sugar level per given unit of time is stable, even after a meal.

In order to solve the above issues, a ketone body concentration estimation device of an aspect according to the present invention includes a processing circuitry configured to perform a process, the process including: acquiring, from a sensor device, a measurement of ketone body concentration measuring ketone bodies excreted from a user; acquiring an elapsed time since the user ate a meal; estimating a stable ketone body concentration, which is a ketone body concentration of when an amount of change in blood sugar level of the user per given unit of time is stable, based on a current measured ketone body concentration and on the elapsed time; and outputting information corresponding to the stable ketone body concentration.

The aspect has the excellent advantageous effect of enabling a ketone body concentration to be estimated when an amount of change in blood sugar level per given unit of time is stable, even after a meal.

BRIEF DESCRIPTION OF THE DRAWINGS

FIG. 3 is a functional block diagram of an acetone concentration estimation device.

FIG. 4 is a flowchart of processing by an acetone concentration estimation program.

FIG. 5 is a graph illustrating an example of an acetone concentration change curve.

FIG. 6 is a diagram for explaining a correction equation to compute an acetone concentration correction amount.

FIG. 7 is a diagram illustrating an example of changes in acetone concentration, blood sugar level, and respiratory quotient.

DETAILED DESCRIPTION

Description follows regarding an exemplary embodiment of the present invention.

Figure 1:
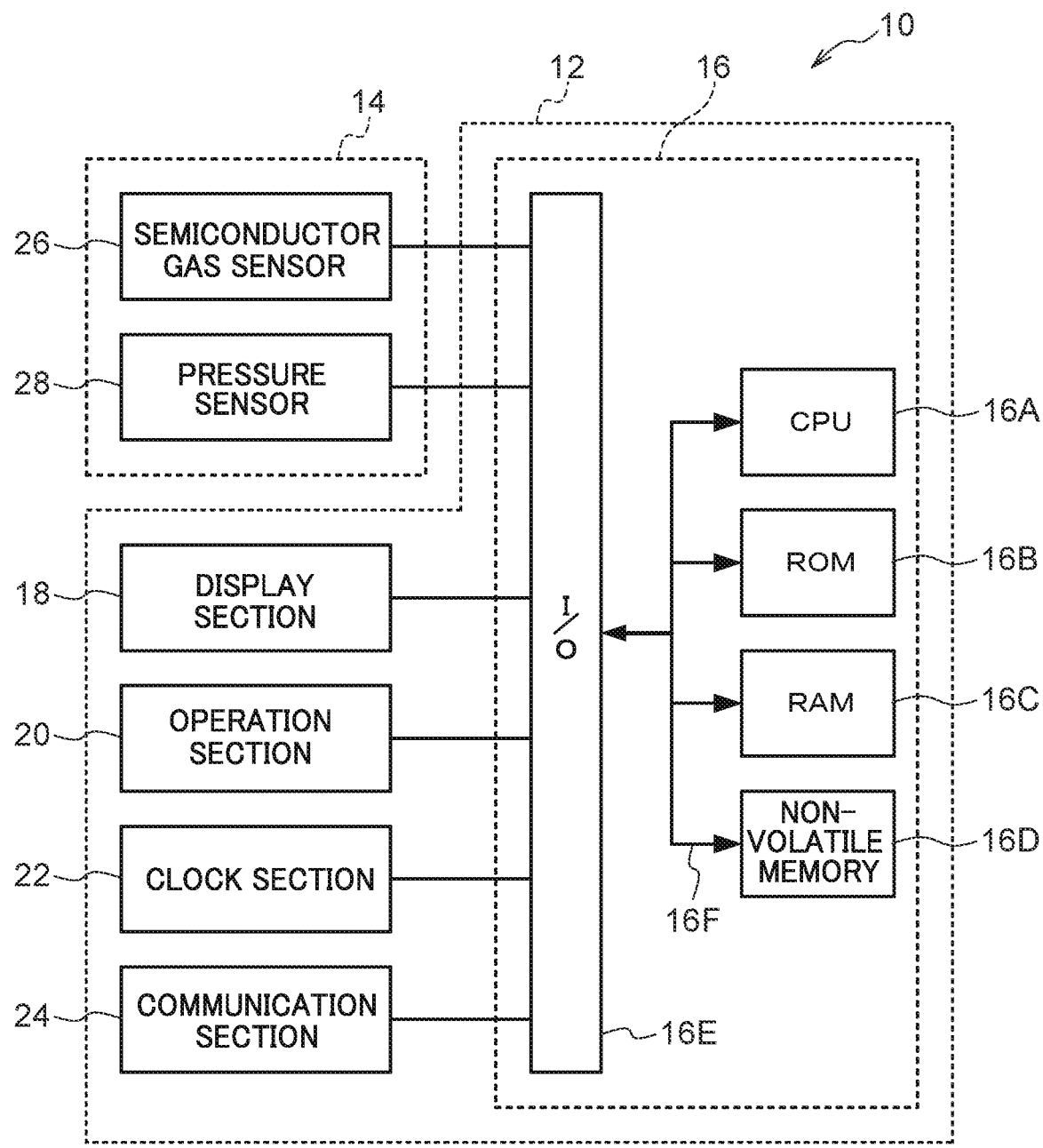
FIG. 1 is a block diagram of an acetone concentration estimation unit.

FIG. 1 is a configuration diagram of an acetone concentration estimation unit 10 according to an exemplary embodiment. As illustrated in FIG. 1, the acetone concentration estimation unit 10 includes an acetone concentration estimation device 12, serving as a ketone body concentration estimation device, and a sensor 14. The acetone concentration estimation device 12 includes a controller 16, a display section 18, an operation section 20, a clock section 22, and a communication section 24. The sensor device 14 includes a semiconductor gas sensor 26 and a pressure sensor 28.

The controller 16 is configured including a central processing unit (CPU) 16A, read only memory (ROM) 12B, random access memory (RAM) 16C, non-volatile memory 16D, and an input-output interface (I/O) 16E, with these being connected together through a bus 16F. In this case, an acetone concentration estimation program that causes the CPU 16A of the controller 16 to execute acetone concentration estimation processing, described later, is executed by, for example, writing the acetone concentration estimation program to the non-volatile memory 16D and reading the acetone concentration estimation program with the CPU 16A. Note that the acetone concentration estimation program may be provided on a recording medium such as a CD-ROM, a memory card, or the like, or may be downloaded from a server, not illustrated in the drawings.

The display section 18, the operation section 20, the clock section 22, the communication section 24, the semiconductor gas sensor 26, and the pressure sensor 28 are connected to the I/O 16E.

The display section 18 is configured by, for example, a liquid crystal panel or the like. Various setting screens, and various result display screens, such as of detection results, for example, are displayed on the display section 18.

The operation section 20 is an operation section for a user to perform various operations.

Note that the display section 18 and the operation section 20 may be configured as a single unit using a touch panel, in a configuration in which operation can be performed by directly touching the touch panel.

The clock section 22 includes a function to acquire the current time, and a timing function to measure time durations.

The communication section 24 includes a function to exchange information with an external device, either by wireless communication or wired communication. Examples of the external device include a non-illustrated body composition analyzer, an activity tracker, and the like.

The acetone concentration estimation device 12 may, for example, be a dedicated device, or may be a general purpose information processing device such as a personal computer, a smartphone, a mobile phone, or a tablet terminal.

The semiconductor gas sensor 26 is a gas sensor having sensitivity to a biological gas such as breath blown thereon by a user. The semiconductor gas sensor 26 detects the biological gas, and outputs the concentration of the detected biological gas as a voltage value. Biological gases in the breath include various types of gases, such as ketone bodies, ethanol, acetaldehydes, hydrogen, water vapor, methane, and various other gases of halitosis. Ketone bodies is a general term for acetoacetic acid, 3-hydroxy butyric acid (β-hydroxybutyric acid), or acetone, and indicates at least one of these.

Specifically, the semiconductor gas sensor 26 includes a metal oxide semiconductor, such as $SnO_2$, a heater, and an electrode. The metal oxide semiconductor has a resistance value that changes when an interfering gas or obtrusive gas is adsorbed. The semiconductor gas sensor 26 lacks gas selectivity and the ability to quantify gas, but has high sensitivity to trace quantities of acetone or the like. In the present exemplary embodiment, a description is given of a case in which a semiconductor gas sensor is used as a sensor for detecting a biological gas. However, the biological gas may be detected using some other device, such as a gas chromatography device.

Note that in the present exemplary embodiment, a description is given of a case in which a biological gas targeted for estimation is acetone. Acetone is a byproduct of metabolizing fat, and the acetone concentration corresponds to the fat burn rate. Fat is not burned when there is a surplus of carbohydrate energy in the body, and so the acetone concentration is low. Fat is burned when there is insufficient carbohydrate energy in the body, and so the acetone concentration rises. This thereby enables the fat burn rate to be known from the acetone concentration.

The pressure sensor 28 detects the pressure of breath being blown thereon by a user. The pressure sensor 28 outputs the magnitude of the detected pressure as a voltage value.

Figure 2:
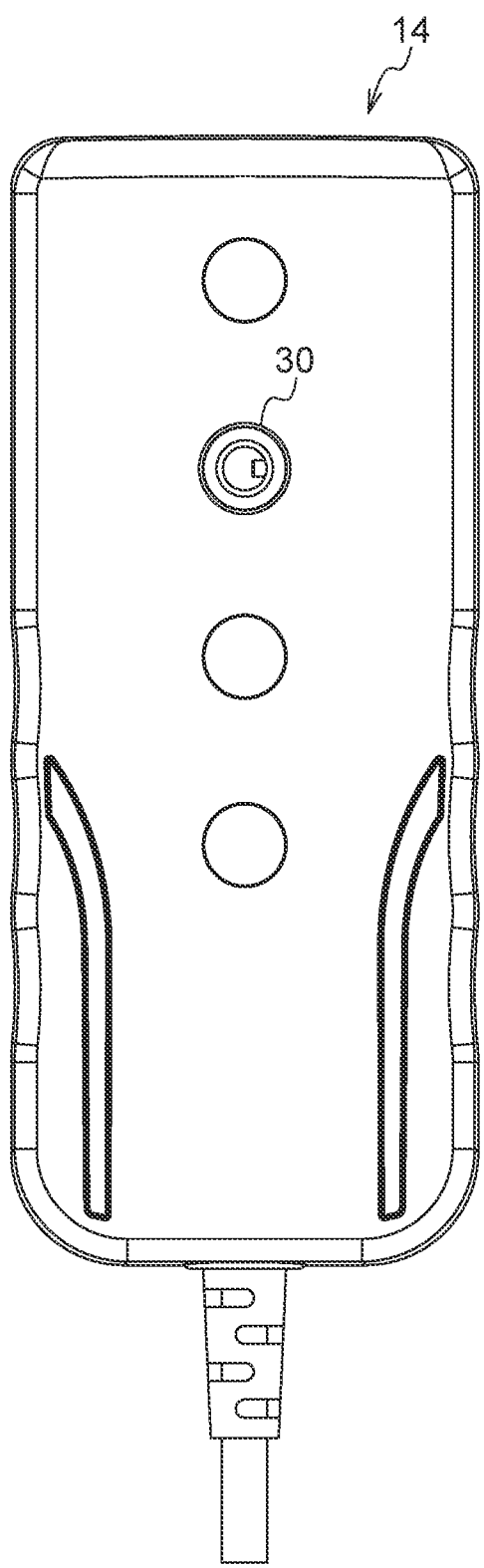
FIG. 2 is an external view of a sensor device.

FIG. 2 illustrates the external appearance of the sensor device 14. As illustrated in FIG. 2, the sensor device 14 includes a mouthpiece 30 for a user to blow breath into. When a user blows their breath into the mouthpiece 30, biological gas is detected by the semiconductor gas sensor 26. Note that although the sensor device 14 illustrated in FIG. 2 is connected to the acetone concentration estimation device 12 by wire, there is no limitation thereto, and the sensor device 14 may be wirelessly connected to the acetone concentration estimation device 12. Further, the sensor device 14 and the acetone concentration estimation device 12 may be formed as a single unit.

As illustrated functionally in FIG. 3, the CPU 16A of the controller 16 includes an acetone concentration acquisition section 40, an elapsed time acquisition section 42, an estimation section 44, and an output section 46. Moreover, the CPU 16A of the controller 16 may further include a functional parameter acquisition section 48.

The acetone concentration acquisition section 40 acquires the acetone concentration measured from the acetone excreted by a user.

The elapsed time acquisition section 42 acquires the time that has elapsed since the user last ate a meal.

The estimation section 44 estimates a stable acetone concentration, this being the acetone concentration of a user when the amount of change in their blood sugar level per given unit of time is stable, based on a current acetone concentration acquired by the acetone concentration acquisition section 40 and an elapsed time acquired by the elapsed time acquisition section 42. Herein, the acetone concentration of when the amount of change in blood sugar level per given unit of time is stable refers to the acetone concentration of when the amount of change in blood sugar level per given unit of time is, for example, a specific value or lower. The acetone concentration before a meal or when the stomach is empty is an example of acetone concentration of when the amount of change in blood sugar level per given unit of time is a specific value or lower.

Specifically, the estimation section 44 estimates the acetone concentration when the amount of change in blood sugar level of a user per given unit of time is stable based on the current acetone concentration acquired by the acetone concentration acquisition section 40, the elapsed time acquired by the elapsed time acquisition section 42, and at least one user-specific parameter.

The at least one user-specific parameter is, for example, acquired by the parameter acquisition section 48. Examples of a user-specific parameter acquired by the parameter acquisition section 48 include physiological parameters, body information, and age. Examples of physiological parameters include carbohydrate intake amount, basal metabolic rate, and active energy expenditure. Examples of body information include body type information. Note that the order of highest impact on estimating acetone concentration is: carbohydrate intake amount, basal metabolic rate, active energy expenditure, body type information, and age.

The output section 46 outputs information corresponding to the acetone concentration of when the amount of change in blood sugar level per given unit of time estimated by the estimation section 44 is stable.

Note that at least one out of the acetone concentration acquisition section 40, the elapsed time acquisition section 42, the estimation section 44, the output section 46, or the parameter acquisition section 48 may be configured by separate hardware such as using an application specific integrated circuit (ASIC).

Next, as operation of the present exemplary embodiment, explanation follows regarding processing by the acetone concentration estimation program executed by the CPU 16A of the controller 16, with reference to the flowchart illustrated in FIG. 4. Note that the processing illustrated in FIG. 4 is executed when a user gives an instruction to execute the acetone concentration estimation program by operating the operation section 20 of the acetone concentration estimation device 12. Note that the processing illustrated in FIG. 4 may be executed upon detecting blowing by a user.

At step S100, the acetone concentration acquisition section 40 displays on the display section 18 a message prompting a user to blow onto the mouthpiece 30, so as have the user blow onto the mouthpiece 30. The acetone concentration acquisition section 40 then acquires an output value of the semiconductor gas sensor 26, namely an acetone concentration α. Note that there are many atmospheric gas components included in breath immediately after the start of blowing. Thus, preferably the end of a breath, when atmospheric gas components have been completely excreted, is utilized when computing the acetone concentration related to the fat burn rate. Namely, the output value of the semiconductor gas sensor 26 is preferably acquired at a timing to obtain the end of a breath. Thus, measuring time with the clock section 22 is preferably started at the point in time when the blowing of a breath is detected, and the output value of the semiconductor gas sensor 26 is preferably acquired at a point in time after a predetermined duration (for example, 4 seconds) has elapsed.

Note that determination as to whether or not a breath has been blown may, for example, be performed by acquiring an output value of the pressure sensor 28 and determining whether or not the acquired output value of the pressure sensor 28 is a predetermined threshold value or greater.

At step S102, the elapsed time acquisition section 42 acquires the time of the most recent meal eaten. Specifically, the elapsed time acquisition section 42 displays, on the display section 18, an input screen for inputting the time of the most recent meal eaten so as to have the user input the time of their most recent meal eaten. Note that a time of the most recent meal eaten input or acquired using an application on another device, such as a smartphone, may be acquired via wireless communication or wired communication.

At step S104, the parameter acquisition section 48 determines whether or not the user will input details regarding the content of their most recent meal. Specifically, parameter acquisition section 48 displays, on the display section 18, a screen asking whether or not the user will input details regarding their most recent meal so as to have the user select whether or not they will input details regarding the content of their most recent meal.

In cases in which the user selects that they will not input details regarding the content of their most recent meal, processing transitions to step S106. On the other hand, in cases in which the user selects that they will input details regarding their most recent meal, processing transitions to step S108. Note that the determination of step S104 may be omitted in cases in which details regarding the content of the most recent meal is acquired in concert with a smartphone application or the like.

At step S106, the parameter acquisition section 48 reads and acquires a carbohydrate intake amount for a predetermined standard meal from the non-volatile memory 16D. Note that configuration may be made such to let user information such as physical build information (such as height and weight), age, sex, etc., of the user be input so as to acquire a carbohydrate intake amount that corresponds with the input user information. In such cases, a data table or computation equation indicating the correspondence relationship between information such as the physical build information, age, sex, etc., and carbohydrate intake amount, may be pre-stored in the non-volatile memory 16D such that a carbohydrate intake amount corresponding to the user information can be acquired using the data table or computation equation. Note that the input or acquired carbohydrate intake amount may be acquired using an application on another device, such as a smartphone, via wireless communication or wired communication.

At step S108, on the other hand, the parameter acquisition section 48 displays, on the display section 18, the input screen for inputting details of a most recent meal so as to have the user input details regarding the content of their most recent meal. The user inputs, for example, the type of meal they ate, the size of the meal, and the like. Note that the input or acquired meal details may be acquired using an application on another device, such as a smartphone, via wireless communication or wired communication.

At step S110, the parameter acquisition section 48 acquires a carbohydrate intake amount based on the meal details input by the user. For example, a data table or computation equation indicating the correspondence relationship between meal type, meal size, and carbohydrate intake amount may be pre-stored in the non-volatile memory 16D such that a carbohydrate intake amount corresponding to the meal details can be acquired using the data table or computation equation.

At step S112, the parameter acquisition section 48 determines whether or not information related to the basal metabolic rate of the user can be acquired. Processing transitions to step S114 in cases in which such information cannot be acquired, and processing transitions to step S116 in cases in which such information can be acquired. Note that information related to basal metabolic rate refers to the basal metabolic rate itself or to body composition information and the like from which the basal metabolic rate can be computed. For example, the parameter acquisition section 48 determines whether or not a body composition analyzer, not illustrated in the drawings, is connected via the communication section 24. If a body composition analyzer is connected, the parameter acquisition section 48 determines that information related to basal metabolic rate can be acquired, and if a body composition analyzer is not connected, the parameter acquisition section 48 determines that information related to basal metabolic rate cannot be acquired.

At step S114, the parameter acquisition section 48 reads and acquires a predetermined, reference basal metabolic rate from the non-volatile memory 16D.

At step S116, on the other hand, the parameter acquisition section 48 acquires information related to basal metabolic rate from the body composition analyzer, and acquires a basal metabolic rate based on the information related to the acquired basal metabolic rate. For example, in cases in which a basal metabolic rate can be acquired directly from the body composition analyzer, the parameter acquisition section 48 may display a message on the display section 18 prompting the user to measure a basal metabolic rate such that they measure a basal metabolic rate, and acquire the measured basal metabolic rate from the body composition analyzer.

Further, in cases in which information necessary for computing a basal metabolic rate, such as the muscle mass of the user, can be acquired from the body composition analyzer, the parameter acquisition section 48 may employ a predetermined computation equation, data table, etc., to find the basal metabolic rate corresponding to the acquired information related to the basal metabolic rate, such as information related to muscle mass.

Further, in cases in which user information such as physical build information (such as height and weight), age, sex, etc. of the user can be acquired via user input or the like, the parameter acquisition section 48 may employ a predetermined computation equation, data table, etc., to find the basal metabolic rate corresponding to the acquired user information.

Further, in cases in which the oxygen consumption rate ($VO_2$) of the user can be acquired via user input or the like, the parameter acquisition section 48 may employ a predetermined computation equation, data table, etc., to find the basal metabolic rate corresponding to the acquired oxygen consumption rate.

Further, in cases in which body fat percentage estimated using at least one out of thickness of subcutaneous fat, waist size, body water weight, height, or weight can be acquired via user input or the like, the parameter acquisition section 48 may employ a predetermined computation equation, data table, etc., to find the basal metabolic rate corresponding to the acquired body fat percentage.

At step S118, the parameter acquisition section 48 determines whether or not information related to energy expenditure of a user during physical activity after eating can be acquired. Processing transitions to step S120 in cases in which such information cannot be acquired, and processing transitions to step S122 in cases in which such information can be acquired. Note that information related to active energy expenditure refers to active energy expenditure itself or to information from which active energy expenditure can be estimated. For example, the parameter acquisition section 48 determines whether or not an activity tracker, not illustrated in the drawings, is connected via the communication section 24. If an activity tracker is connected, the 38 determines that active energy expenditure can be acquired, and if an activity tracker is not connected, the parameter acquisition section 48 determines that information related to active energy expenditure cannot be acquired. Note that an activity tracker is a device that is capable of acquiring a number of steps walked, amount of exercise, etc., of a user.

At step S120, the parameter acquisition section 48 reads and acquires a predetermined, reference active energy expenditure from the non-volatile memory 16D. The reference active energy expenditure may be taken as the active energy expenditure when, for example, the user is engaged in deskwork at work; however, there is no limitation thereto. The reference active energy expenditure may, for example, be selected according to occupation, the nature of the work, or by some other breakdown.

At step S122, on the other hand, the parameter acquisition section 48 acquires information related to energy expenditure from the activity tracker, and acquires an active energy expenditure based on the acquired information related to active energy expenditure. For example, in cases in which active energy expenditure can be acquired directly from the activity tracker, the parameter acquisition section 48 may acquire active energy expenditure from the activity tracker.

In cases in which a number of steps walked after eating can be acquired from a pedometer, the parameter acquisition section 48 may, for example, employ a predetermined computation equation, a data table, etc., to find the active energy expenditure corresponding to the acquired number of steps walked.

At step S124, the estimation section 44 computes an acetone concentration correction amount in order to compute acetone concentration of when the amount of change in blood sugar level per given unit of time is stable, for example, the acetone concentration of the user before a meal (or the acetone concentration when the stomach is empty). Specifically, the estimation section 44 uses the correction equation in the following equation to compute an acetone concentration correction amount E based on an elapsed time A, which is from the most recent meal eaten acquired at step S102, a carbohydrate intake amount B acquired at step S106 or step S110, a basal metabolic rate C acquired at step S114 or step S116, and an active energy expenditure D acquired at step S120 or step S122.

$$E = f(A) - f(B, C, D) \quad (1)$$

Here, f(A) is a function in which acetone concentration is found in terms of the parameter elapsed time A, and may, for example, be a function representing a reference change curve K1 as illustrated by the solid line in FIG. 5. Further, f(B, C, D) is a function in which acetone concentration is found in terms of the parameters carbohydrate intake amount B, basal metabolic rate C, and active energy expenditure D.

Note that as illustrated in FIG. 5, the reference change curve K1 is a reference curve of change in acetone concentration after eating a meal; however, in cases in which the carbohydrate intake amount is small, the basal metabolic rate is high, and/or the active energy expenditure is high, the change curve of the acetone concentration becomes like change curve K2, the change curve K2 having a smaller degree of decrease in acetone concentration than the reference change curve K1. Further, in cases in which the carbohydrate intake amount is large, the basal metabolic rate is low, and/or the active energy expenditure is low, the change curve of the acetone concentration becomes like the change curve line K3 having a larger degree of decrease in acetone concentration than the reference change curve K1.

Therefore, for Equation 1, an equation is selected corresponding to the carbohydrate intake amount B, the basal metabolic rate C, and the active energy expenditure D. As illustrated in FIG. 6, for example, in the case of the function f(A), this being a function in which acetone concentration found corresponding to the elapsed time A corresponds to the reference change curve K1, the carbohydrate intake amount B and the basal metabolic rate C are divided into the three levels of "low", "medium", and "high", and active energy expenditure D is divided into five levels corresponding to comparisons with threshold values ×4 to ×8. A correction equation is selected according to the values of the carbohydrate intake amount B, the basal metabolic rate C, and the active energy expenditure D.

For example, when the carbohydrate intake amount B is "low", the basal metabolic rate C is "low", and the active energy expenditure D is less than the threshold value ×4, the correction equation f(A)−f1(B, C, D) is selected. The selected correction equation is used to compute the correction amount E.

At step S126, the estimation section 44 uses the following equation to compute a pre-meal acetone concentration β based on the current acetone concentration α acquired at step S100 and the acetone concentration correction amount E computed at step S124, and the output section 46 displays the pre-meal acetone concentration β on the display section 18.

$$\beta = \alpha + E \quad (2)$$

Namely, as illustrated in FIG. 7, the pre-meal acetone concentration β is computed by adding the correction amount E to the acetone concentration α, this being the acetone concentration at a current point in time tA after time A has elapsed since a point in time t1 of when a meal was eaten. The computed acetone concentration β is displayed on the display section 18. Note that in addition to the acetone concentration change curve, FIG. 7 illustrates a blood sugar level change curve and a bar graph of the respiratory quotient RQ.

At step S128, as illustrated in FIG. 7, the estimation section 44 uses the following equation to compute a time tx that is from the current time until the acetone concentration returns to a value of when the amount of change in blood sugar level per given unit of time is stable (for example, in a state of an empty stomach or before a meal), and the output section 46 displays the time tx on the display section 18.

$$tx = fx(A, B, C, D) \quad (3)$$

fx(A, B, C, D) is a function for computing time tx, this being the time until the acetone concentration returns to a value of when the amount of change in blood sugar level per given unit of time is stable, and takes elapsed time A since eating a meal, carbohydrate intake amount B, basal metabolic rate C, and active energy expenditure D as parameters. Note that the function for computing time tx may take only elapsed time A as a parameter.

At step S130, as illustrated in FIG. 7, the estimation section 44 uses the following equation to compute a fat burning start time ty, this being the time from the current point in time until a time at which fat starts to be burned, and the output section 46 displays the time ty on the display section 18. Note that the fat burning start time is the time until the acetone concentration returns to an acetone concentration y at which it can be determined that fat burning will start.

$$ty = fy(A, B, C, D) \quad (4)$$

fy(A, B, C, D) is a function for computing the fat burning start time ty that takes elapsed time A since eating a meal, carbohydrate intake amount B, basal metabolic rate C, and active energy expenditure D as parameters. Note that the function for computing time ty may take only elapsed time A as a parameter.

At step S132, as illustrated in FIG. 7, the estimation section 44 uses the following equation to compute a current blood sugar level H, and the output section 46 displays the blood sugar level H on the display section 18.

$$H = fh(A, B, C, D) \quad (5)$$

fh(A, B, C, D) is a function for computing the blood sugar level H that takes elapsed time A since eating a meal, carbohydrate intake amount B, basal metabolic rate C, the active energy expenditure D as parameters. Note that the function for computing blood sugar level H may take only elapsed time A as a parameter.

Thus, in the present exemplary embodiment, in addition to the elapsed time A since a meal was eaten, the pre-meal acetone concentration can be computed based on the carbohydrate intake amount B, the basal metabolic rate C, and the active energy expenditure D, which are user-specific parameters. Thus, even in cases in which a meal has been eaten, it is possible to obtain a post-meal measurement result equivalent to that of a pre-meal measurement result without needing to wait a long time before taking a measurement.

Moreover, in the present exemplary embodiment, a return time, which is the time from the current point in time until the amount of change in blood sugar level of a user per given unit of time returns to a stable state, is estimated and displayed. It is thus possible to ascertain the timing at which the energy from the most recent eaten meal will be completely used up, and a course of action formed in the interim. This gives a basis for determining a course of action in such an interim, such as increasing physical activity level, and adjusting the time at which the next meal will be eaten or the content of the next meal.

Moreover, in the present exemplary embodiment, the fat burning start time, this being the time from the current point in time until a time at which fat of a user starts to be burned, is estimated and displayed. It is thus possible to easily ascertain the time until fat metabolization comes into effect.

Moreover, in the present exemplary embodiment, the current blood sugar level is estimated and displayed, enabling carbohydrate intake to be suitably determined.

Further, restrictions on measurement timing are removed, enabling measuring as desired, thus broadening the suitable range/applicable range of nutritional guidance and weight loss guidance advice, and enabling various types of applications to be readily utilized. Moreover, estimates can be made for the time until the amount of change in blood sugar level of a user per given unit of time returns to a stable state, the fat burning start time until fat starts to be burned, and blood sugar level. Thus, how much time until fat metabolization comes into effect, and how much time it takes for the acetone concentration to become the same value as of when the amount of change in blood sugar level of a user per given unit of time is in the stable state, etc., can be easily determined, making it possible to easily ascertain the next suitable time for eating.

Note that in the present exemplary embodiment, explanation has been given of a case in which, in addition to the elapsed time A, the carbohydrate intake amount of the user, the basal metabolic rate of the user, and the active energy expenditure of the user are all employed as parameters to estimation acetone concentration before a meal. However, in addition to the elapsed time A, one or two out of the carbohydrate intake amount of the user, the basal metabolic rate of the user, or the active energy expenditure of the user may be employed as parameters to estimate acetone concentration before a meal.

In the present exemplary embodiment, the ketone body concentration of when the amount of change in blood sugar level per given unit of time is stable (stable ketone body concentration) is estimated. However, as an alternative thereto, the ketone body concentration of when both the blood sugar level is a specific value or lower and the amount of change in blood sugar level per given unit of time is stable (low-value stable ketone body concentration) may be estimated. Moreover, the time tx from the current point in time until the acetone concentration returns to a value of when the amount of change in blood sugar level per given unit of time is a stable value, as determined by the estimation section 44 at step S128, may be configured as a time from the current point in time until both the blood sugar level is a specific value or lower and the acetone concentration returns to a value of when the amount of change in blood sugar level per given unit of time is stable. Doing so enables ketone body concentration to be estimated in a state in which the blood sugar level is sufficiently low, namely, closer to a state in which the stomach is empty.

What is claimed is:

1. A device comprising:
   processing circuitry configured to perform a process, the process including:
   detecting, using a sensor device at a current point in time, a current measurement of ketone body concentration measuring ketone bodies excreted from a user, wherein the current measurement of ketone body concentration represents a post-meal ketone body concentration after the user ate a meal;
   detecting an elapsed time since the user ate a meal, the elapsed time being a time period from a point in time when the user ate a meal to the current point in time;
   detecting at least one user-specific parameter including at least one of a carbohydrate intake amount, a basal metabolic rate and an active energy expenditure of the user;

determining a ketone body concentration correction amount using the elapsed time and the at least one user-specific parameter;
estimating a stable ketone body concentration based on the current measured ketone body concentration and the ketone body concentration correction amount, wherein the stable ketone body concentration represents a pre-meal ketone body concentration of when an amount of change in blood sugar level of the user per given unit of time is stable; and
outputting information corresponding to the stable ketone body concentration.

2. The device of claim 1, wherein the process further includes:
estimating a return time, which is a period from the current point in time until the amount of change in the blood sugar level of the user per given unit of time returns to a stable state, based on the current measured ketone body concentration, the elapsed time, and the at least one user-specific parameter; and
outputting information corresponding to the return time.

3. The device of claim 1, wherein the process further includes:
estimating a fat burning start time, which is a period from the current point in time until fat of the user starts to be burned, based on the current measured ketone body concentration, the elapsed time, and the at least one user-specific parameter; and
outputting information corresponding to the fat burning start time.

4. The device of claim 2, wherein the process further includes:
estimating a fat burning start time, which is a period from the current point in time until fat of the user starts to be burned, based on the current measured ketone body concentration, the elapsed time, and the at least one user-specific parameter; and
outputting information corresponding to the fat burning start time.

5. The device of claim 1, wherein the process further includes:
estimating a current blood sugar level of the user, based on the current measured ketone body concentration, the elapsed time, and the at least one user-specific parameter; and
outputting information corresponding to the current blood sugar level of the user estimated.

6. The device of claim 2, wherein the process further includes:
estimating a current blood sugar level of the user, based on the current measured ketone body concentration, the elapsed time, and the at least one user-specific parameter; and
outputting information corresponding to the current blood sugar level of the user estimated.

7. The device of claim 3, wherein the process further includes:
estimating a current blood sugar level of the user, based on the current measured ketone body concentration, the elapsed time, and the at least one user-specific parameter; and
outputting information corresponding to the current blood sugar level of the user estimated.

8. The device of claim 4, wherein the process further includes:
estimating a current blood sugar level of the user, based on the current measured ketone body concentration, the elapsed time, and the at least one user-specific parameter; and
outputting information corresponding to the current blood sugar level of the user estimated.

9. The device of claim 1, wherein the ketone body concentration correction amount is determined using time-series data corresponding to the elapsed time and time-series data corresponding to the at least one user-specific parameter.

10. A detection method comprising:
detecting, using a sensor device at a current point in time, a current measurement of ketone body concentration measuring ketone bodies excreted from a user, wherein the current measurement of ketone body concentration represents a post-meal ketone body concentration after the user ate a meal;
detecting an elapsed time since the user ate a meal, the elapsed time being a time period from a point in time when the user ate a meal to the current point in time;
detecting at least one user-specific parameter including at least one of a carbohydrate intake amount, a basal metabolic rate and an active energy expenditure of the user;
determining a ketone body concentration correction amount using the elapsed time and the at least one user-specific parameter;
estimating a stable ketone body concentration based on the current measured ketone body concentration and the ketone body concentration correction amount, wherein the stable ketone body concentration represents a pre-meal ketone body concentration of when an amount of change in blood sugar level of the user per given unit of time is stable; and
outputting information corresponding to the stable ketone body concentration.

11. The method of claim 10, further comprising:
estimating a fat burning start time, which is a period from the current point in time until fat of the user starts to be burned, based on the current measured ketone body concentration, the elapsed time, and the at least one user-specific parameter; and
outputting information corresponding to the fat burning start time.

12. The method of claim 11, further comprising:
estimating a current blood sugar level of the user, based on the current measured ketone body concentration, the elapsed time, and the at least one user-specific parameter; and
outputting information corresponding to the current blood sugar level of the user estimated.

13. The method of claim 10, further comprising:
estimating a current blood sugar level of the user, based on the current measured ketone body concentration, the elapsed time, and the at least one user-specific parameter; and
outputting information corresponding to the current blood sugar level of the user estimated.

14. The method of claim 10, wherein the ketone body concentration correction amount is determined using time-series data corresponding to the elapsed time and time-series data corresponding to the at least one user-specific parameter.

15. A non-transitory computer-readable storage medium storing a ketone body concentration estimation program executable to cause processing circuitry to perform processing, the processing comprising:
- detecting, using a sensor device at a current point in time, a current measurement of ketone body concentration measuring ketone bodies excreted from a user, wherein the current measurement of ketone body concentration represents a post-meal ketone body concentration after the user ate a meal;
- detecting an elapsed time since the user ate a meal, the elapsed time being a time period from a point in time when the user ate a meal to the current point in time;
- detecting at least one user-specific parameter including at least one of a carbohydrate intake amount, a basal metabolic rate and an active energy expenditure of the user;
- determining a ketone body concentration correction amount using the elapsed time and the at least one user-specific parameter;
- estimating a stable ketone body concentration based on the current measured ketone body concentration and the ketone body concentration correction amount, wherein the stable ketone body concentration represents a pre-meal ketone body concentration of when an amount of change in blood sugar level of the user per given unit of time is stable; and
- outputting information corresponding to the stable ketone body concentration.

16. The non-transitory computer-readable storage medium of claim 15, the processing further comprising:
- estimating a fat burning start time, which is a period from the current point in time until fat of the user starts to be burned, based on the current measured ketone body concentration, the elapsed time, and the at least one user-specific parameter; and
- outputting information corresponding to the fat burning start time.

17. The non-transitory computer-readable storage medium of claim 16, the processing further comprising:
- estimating a current blood sugar level of the user, based on the current measured ketone body concentration, the elapsed time, and the at least one user-specific parameter; and
- outputting information corresponding to the current blood sugar level of the user estimated.

18. The non-transitory computer-readable storage medium of claim 15, the processing further comprising:
- estimating a current blood sugar level of the user, based on the current measured ketone body concentration, the elapsed time, and the at least one user-specific parameter; and
- outputting information corresponding to the current blood sugar level of the user estimated.

19. The non-transitory computer-readable storage medium of claim 15, wherein the ketone body concentration correction amount is determined using time-series data corresponding to the elapsed time and time-series data corresponding to the at least one user-specific parameter.

* * * * *